United States Patent [19]

Telorack

[11] Patent Number: 4,752,947
[45] Date of Patent: Jun. 21, 1988

[54] PRIMARY RADIATION DIAPHRAGM FOR X-RAY EXAMINATION DEVICES

[75] Inventor: Gerhard Telorack, Aurachtal, Fed. Rep. of Germany

[73] Assignee: Siemens Aktiengesellschaft, Berlin and Munich, Fed. Rep. of Germany

[21] Appl. No.: 801,324

[22] Filed: Nov. 25, 1985

[30] Foreign Application Priority Data

Dec. 3, 1984 [DE] Fed. Rep. of Germany ....... 3444058

[51] Int. Cl.$^4$ ............................................. G21K 1/04
[52] U.S. Cl. ..................................... 378/152; 378/150; 378/153
[58] Field of Search ......................... 378/150, 152, 153

[56] References Cited

U.S. PATENT DOCUMENTS

| 3,631,249 | 7/1969 | Friede . | |
|---|---|---|---|
| 3,937,966 | 2/1976 | Godel et al. | 378/191 |
| 3,980,407 | 5/1976 | Hill . | |
| 4,463,266 | 7/1984 | Brahme | 378/150 |
| 4,489,426 | 12/1984 | Grass et al. | 378/150 |
| 4,534,052 | 8/1985 | Milcamps | 378/150 |
| 4,672,652 | 6/1987 | Hüttenrauch et al. | 378/151 |

FOREIGN PATENT DOCUMENTS 2842659 4/1980 Fed. Rep. of Germany ...... 378/150

Primary Examiner—Janice A. Howell
Assistant Examiner—David P. Porta
Attorney, Agent, or Firm—Hill, Van Santen, Steadman & Simpson

[57] ABSTRACT

A primary radiation diaphragm for X-ray examination devices has at least one pair of diaphragm plates movable in opposite directions relative to each other for gating an X-ray beam. The diaphragm plates are displaceably mounted in spaced planes and the respective adjustment limits are selected such that each diaphragm plate can selectively limit the X-ray beam with one of two edges disposed perpendicular to the path of adjustment movement. The edges may have different shapes for adapting the gated field to the shape of the body organ under examination.

3 Claims, 2 Drawing Sheets

PRIMARY RADIATION DIAPHRAGM FOR X-RAY EXAMINATION DEVICES

BACKGROUND OF THE INVENTION

1. Field of the Invention

The present invention relates to a primary radiation diaphragm for X-ray examination devices, and in particular to such a radiation diaphragm having at least one pair of diaphragm plates adjustable in opposite directions relative to each other.

2. Description of the Prior Art

A primary radiation diaphragm having two diaphragm plates movable in opposite directions relative to each other for limiting the extent of an X-ray beam is described in German OS 1,800,879. In this known radiation diaphragm, the edges of the adjustable plates are wedge-shaped so that the x-radiation is not completely absorbed by the diaphragm at the region close to the edge thereof. This serves two purposes. First, a good gating of the diagnostically relevant image region is possible, so that substantially no image regions not containing useful image information are bright enough to interfere with viewing of the relevant image. Second, when using a picture reproduction device, such as a monitor, for introducing instruments into the examination subject, it is assured that the instrument can be seen before entry into the diagnostically relevant region.

In this known primary radiation diaphragm, the diaphragm edges limiting the X-ray beam are straight. In practice, such a straight edge does not always correspond to the desired limitation of the image field. Particularly, for gating the regions surrounding the heart, a curved edge contour is desirable so that the image field can be optimally adapted to the shape of the heart.

A diaphragm system having plates with differently shaped edges which can be moved above each other is described in USLP 3,980,407. Different shapes at the gated field can be achieved using the same diaphragm plates in this manner.

SUMMARY OF THE INVENTION

It is an object of the present invention to provide a primary radiation diaphragm which permits a plurality of different image field shapes to be achieved by the use of two diaphragm plates.

It is a further object of the present invention to provide a primary radiation diaphragm which permits rectangular gating as well as gating corresponding to the heart contour using the same set of plates as may optionally be needed.

Another object of the present invention is to provide such a primary radiation diaphragm which is capable of individual adaptation for examination of respective patients.

The above objects are achieved in accordance with the system disclosed herein wherein the diaphragm plates are adjustably mounted in two spaced planes and the path of adjustment is selected large enough such that the X-ray beam is optionally limitable by each diaphragm plate with one of two edges disposed perpendicular to the path of movement during adjustment. Individual adjustment means are provided for each of the diaphragm plates. In the primary radiation diaphragm described herein, the diaphragm plates are arranged in pairs, with the plates in each pair being capable of movement past each other over each other, so that different shapes of gating are possible by selective use of the different shaping of the two edges of a single diaphragm plate. These edges are disposed perpendicular to the path of adjustment movement of the plates.

DESCRIPTION OF THE PREFERRED EMBODIMENTS

Figure 1:
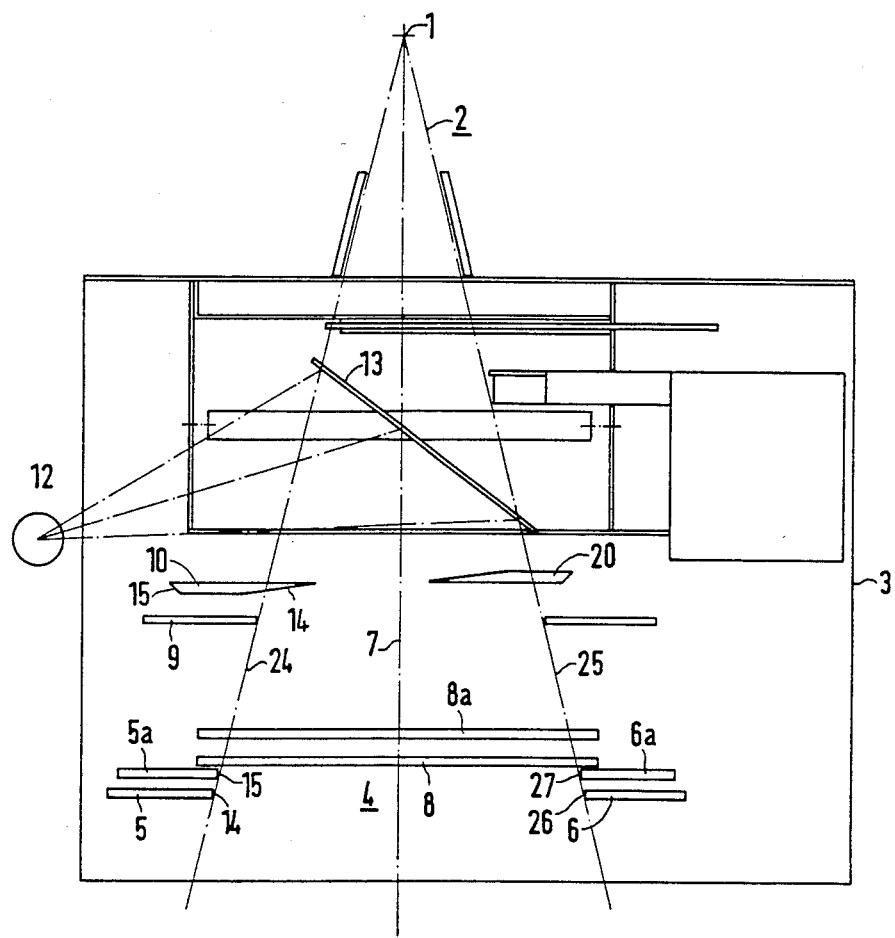
FIG. 1 is a side view of a primary radiation diaphragm constructed in accordance with the principles of the present invention.

A primary radiation diaphragm 3 is shown in FIG. 1 for use in gating an X-ray beam 2 generated at an X-ray focus, schematically indicated at 1. The primary diaphragm 3 includes a rectangular diaphragm system 4 having a pair of diaphragm plates 5 and 6 disposed in a plane and adjustable in opposite directions relative to each other, and another pair of diaphragm plates 5a and 6a disposed in a plane spaced from the plane containing the plates 5 and 6, the plates 5a and 6a also being mounted for adjustable movement in opposite directions relative to each other. The upper diaphragm plates 5a and 6a are synchronously moved in combination to a slightly greater extent then are the plates 5 and 6 with respect to a central ray 7 of the X-ray beam 2 so as to permit, if needed, diverging of the beam 2 as indicated in FIG. 1. Two further pairs of diaphragm plates are also included within the diaphragm system 4 movable in opposite directions which are perpendicular to the directions of movement of the diaphragm pairs 5a and 6a and the diaphragm pair 5 and 6. One plate 8 and one plate 8a of these additional pairs of plates are shown in FIG. 1. The plates 8 and 8a, and the corresponding plates in each pair (not shown) limit the extent of the X-ray beam 2 in a direction perpendicular to the plane of FIG. 1.

The primary diaphragm 3 also includes an iris diaphragm 9 disposed in front of the rectangular diaphragm system 4 in the direction of beam propagation. The iris diaphragm 9 adapts the shape of the X-ray beam 2 to the shape of the input luminescent screen of an X-ray image intensifier (not shown) by inserting wedges at the corners of the rectangular diaphragm system 4, as needed.

Figure 2:
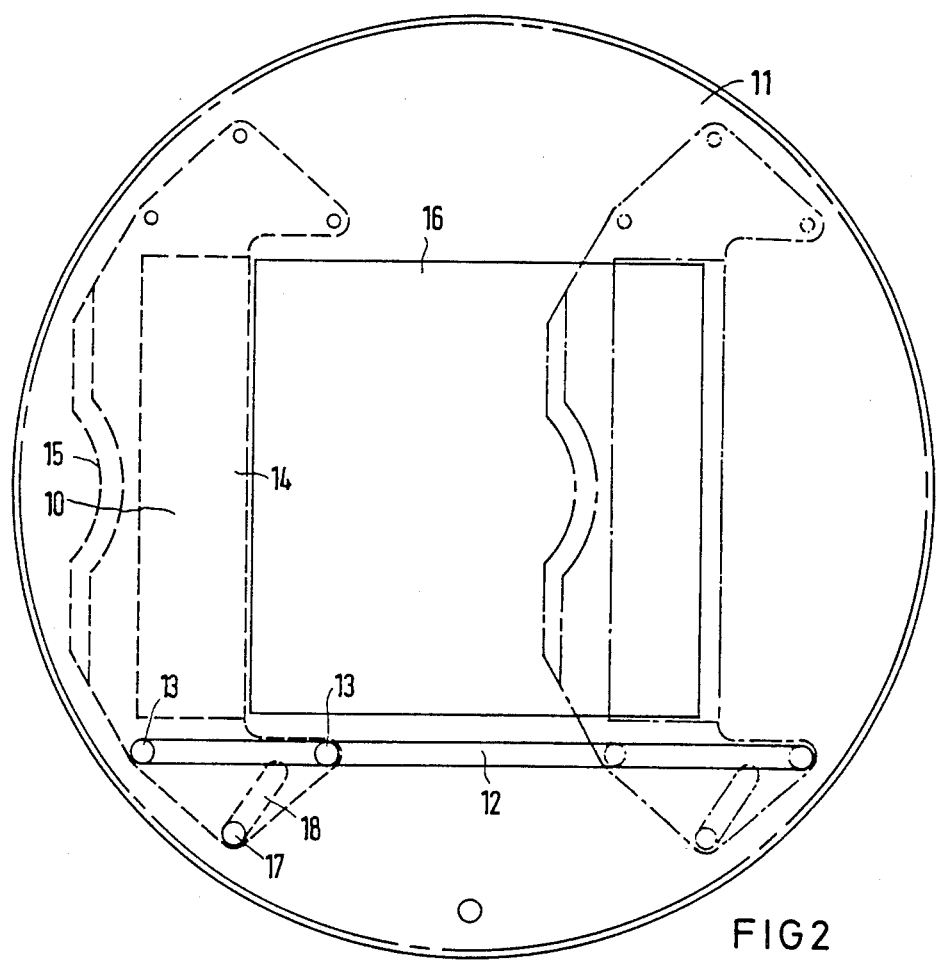
FIG. 2 is a plan view of a portion of the primary radiation diaphragm shown in FIG. 1 showing one of the adjustable plates.
Figure 3:
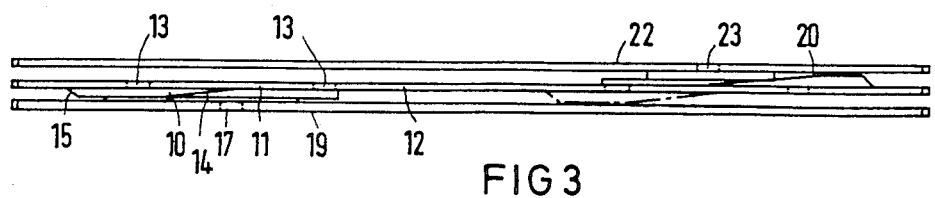
FIG. 3 is a side view in further detail of a portion of the primary radiation diaphragm shown in FIG. 1.

Two diaphragm plates 10 and 20 are shown in FIG. 3 with the surrounding parts and mountings omitted for clarity. Those details are shown in FIGS. 2 and 3 discussed below. The diaphragm plates 10 and 20 are adjustable in opposite directions relative to the central ray 7 in two different parallel planes so that the plates 10 and 20 can be moved past each other over each other. The path of adjustment of the diaphragm plates 10 and 20 is thus large enough so that each diaphragm plate 10 and 20 can selectively limit the X-ray beam 2 with one of its two edges, those two edges being disposed perpendicular to the path of adjustment of the plates. For example, diaphragm plate 10 has a left edge 15 which may be selectively contoured, and a right edge 14, which may be straight.

The primary radiation diaphragm 3 also has a light sight including a light source 12 and a mirror 13 which is transmissive for x-radiation. The mirror 13 generates a visible light field which is coextensive with the X-ray field so that the extent of the gated X-ray field can be seen on the examination subject.

The gating of the X-ray beam 2 by the diaphragm plates 10 and 20 is achieved as more clearly seen in FIGS. 2 and 3. In FIG. 2, more clarity only the left diaphragm plate 10 is shown. The plate 10 is shown at a left extreme position in dashed lines and at a right extreme position in dot and dashed lines in FIG. 2. A diaphragm plate 10 is mounted on an annular disc 11 and is displaceable along a slot 12 in the disc 11. The plate 10 is guided in the slot 12 by two pegs 13. The slot 12 is of a length such that the X-ray beam 2 can be optionally limited by the straight right edge 14 of the plate 10, or by the curved left edge 15 of the diaphragm plate 10. The maximum diaphragm aperture is defined by a rectangular opening 16 in the disc 11. As can be seen in FIGS. 2 and 3, the diaphragm plate 10 can be moved from the left extreme position to the right extreme position, in which case the curved edge 15 limits the X-ray beam 2. The different shapes of edges and 14 permit the gated field to similarly exhibit a different shape, dependent upon the position of the diaphragm plate 10. The edge 15 functions to gate the beam to a shape corresponding to the heart contour, and as stated above, is curved for this purpose. The edge 14 is a straight line. In a known manner, the diaphragm plate 10 is bevelled at its regions close to the edge, and is thus partially transparent to x-radiation. The diaphragm plate 20 (not shown in FIG. 2) is a mirror image of the plate 10.

Adjustment of the diaphragm plate 10 (as well as the plate 20 by a similar mechanism) is undertaken by a pin 17 mounted to the plate 10 which is moved in an oblong opening of a disc 19 disposed beneath the disc 11. The disc 19, as well as a disc 22 disposed above the disc 11, has a central opening for defining the maximum field size. The disc 22 has not been shown in FIG. 2. The disc 22 also has a radial slot, in which a pin 23 of the diaphragm 20 is displaceably guided.

For adjusting the diaphragm plates 10 and 20, a relative rotation of the discs 19 and 22 relative to the disc 11 is undertaken. When all three discs 11, 19 and 22 are rotated congruently and synchronously, the position of the gated slot is also rotated. The discs 11, 19 and 22 are provided with outside denticulation, schematically indicated by the dashed line inside the circumference of the disc 11 in FIG. 2, so as to be individually or synchronously rotated. The pins 17 and 23 are mounted to shoulders of the diaphragm plates 10 and 20. The shoulders are bent downwardly or upwardly at right angles to the remainder of the plates.

The diaphragm plates 10 and 20 can be moved completely past one another so as to selectively limit the X-ray beam 2 with one of the two edges of the plates. These are the two edges referenced 14 and 15 for the diaphragm plate 10. As stated above, the diaphragm plate 20 is a mirror image of the diaphragm plate 10, that is, the straight edge is at the left in the position shown in FIG. 3, and the edge matched to the heart contour is at the right as shown in FIG. 3.

Although modifications and changes may be suggested by those skilled in the art it is the intention of the inventor to embody within the patent warranted hereon all changes and modificatons as reasonably and properly come within the scope of their contribution to the art.

I claim as invention:

1. A primary radiation diaphragm for an X-ray apparatus having an X-ray beam, comprising:
   at least one pair of diaphragm plates respectively disposed in spaced parallel planes, the plates of each pair having opposite side edges; and
   means for individually adjusting the position of each of said diaphragm plates with respect to said x-ray beam by moving said plates in said planes in directions opposite to each other to a location along a path movement of sufficient length such that either one of said opposite edges of the plates of each pair can selectively limit said X-ray beam, said means including a central disk having a central rectangular opening therein through which said X-ray beam radiates, and having two slots therein respectively receiving pegs extending from said diaphragm plates, an upper disk disposed above said central disk and having a slot disposed at an angle relative to said slots in said central disk for receiving a pin extending from one of said plates, said upper disk having a central opening co-extensive with said central opening in said central disk, and a lower disk disposed between said central disk and having a slot therein disposed at an angle relative to the slots in said central disk for receiving a pin from the other of said plates, said lower disk having a central opening therein co-extensive with said central opening in said central disk, said upper, central and lower disks being individually rotatable relative to each other and synchronized with each other for moving said plates through said slots for selectively covering portions of said central openings in said disks.

2. The primary radiation diaphragm of claim 1 wherein at least one of said opposite side edges is a straight edge.

3. A primary radiation diaphragm as claimed in claim 1 wherein at least one of said opposite side edges is curved.

* * * * *